US006638742B1

(12) United States Patent
Hoffman

(10) Patent No.: US 6,638,742 B1
(45) Date of Patent: Oct. 28, 2003

(54) METHODS FOR OBTAINING TAXANES

(75) Inventor: Angela Hoffman, Beaverton, OR (US)

(73) Assignee: University of Portland, Portland, OR (US)

( * ) Notice: Subject to any disclaimer, the term of this patent is extended or adjusted under 35 U.S.C. 154(b) by 0 days.

(21) Appl. No.: 09/900,077

(22) Filed: Jul. 6, 2001

Related U.S. Application Data

(60) Provisional application No. 60/216,863, filed on Jul. 7, 2000.

(51) Int. Cl.[7] .............................. C12P 17/02; C12N 1/14
(52) U.S. Cl. ....................... 435/123; 435/118; 435/132; 435/147; 435/155; 435/171; 435/252.1; 435/254.1; 435/911; 549/510; 549/511
(58) Field of Search ........................... 435/254.1, 252.1, 435/118, 123, 132, 147, 155, 171, 911; 549/510, 511

(56) References Cited

U.S. PATENT DOCUMENTS

| | | | |
|---|---|---|---|
| 4,206,221 A | 6/1980 | Miller et al. | |
| 4,468,458 A | 8/1984 | Sato et al. | |
| 4,814,470 A | 3/1989 | Colin et al. | |
| 4,857,653 A | 8/1989 | Colin et al. | |
| 4,924,011 A | 5/1990 | Denis et al. | |
| 4,942,184 A | 7/1990 | Haugwitz et al. | |
| 4,960,790 A | 10/1990 | Stella et al. | |
| 5,019,504 A | 5/1991 | Christen et al. | |
| 5,202,448 A | 4/1993 | Carver et al. | |
| 5,232,684 A | 8/1993 | Blumberg et al. | |
| 5,243,045 A | 9/1993 | Holton et al. | |
| 5,322,779 A | 6/1994 | Strobel et al. | |
| 5,445,809 A | 8/1995 | Strobel et al. | |
| 5,451,392 A | 9/1995 | Strobel et al. | |
| 5,670,663 A | 9/1997 | Durzan et al. | |
| 5,861,302 A | 1/1999 | Stierle et al. | |
| 5,908,759 A | 6/1999 | Stierle et al. | |
| 5,916,783 A | 6/1999 | Stierle et al. | |
| 5,958,741 A | 9/1999 | Stierle et al. | |
| 5,981,777 A | 11/1999 | Durzan et al. | |
| 6,013,493 A | 1/2000 | Stierle et al. | |
| 6,030,818 A | 2/2000 | Page et al. | |
| 6,043,072 A | 3/2000 | Croteau et al. | |
| 6,066,748 A | 5/2000 | Han et al. | |
| 6,329,193 B1 * | 12/2001 | Strobel et al. | ............ 435/254.1 |

OTHER PUBLICATIONS

Strobel et al, J. Industrial Microbiol. 17: 417–423, 1996.*
Kim et al, Agric. Chem. Biotechnol. 42(2):97–99, 1999.*
Difco Laboratories (1953), Difco Manual of Dehydrated Culture Media and Reagents for Microbiological and Clinical Laboratory Procedures, 9th ed., pp. 64–65 and 242–246. Difco Laboratories, Detroit, Michigan, at least as early as 1953.

M.C. Wani, W.H. Taylor, M.E. Wall, P. Coggon, A.T. McPhail, Plant Antitumor Agents. VI. The Isolation and Structure of Taxol, a Novel Antileukemic and Antitumor Agent from Taxus brevifolia, J. Am. Chem. Soc., vol. 93, pp. 2325–2327, American Chemical Society, at least as early as May 5, 1971.

A. Stierle, G. Strobel, D. Stierle, Taxol and Taxane Production by Taxomyces andreanae, an Endophytic Fungus of Pacific Yew, Science, vol. 260, pp. 214–216, the American Association for the Advancement of Science, at least as early as Apr. 9, 1993.

A. Stierle, D. Stierle, G. Strobel, G. Bignami, P. Grothaus, Bioactive Metabolites of the Endophytic Fungi of Pacific Yew, Taxus brevifolia, Paclitaxel, Taxanes, and Other Bioactive Compounds, In: Taxane Anticancer Agents: Basic Science and Current Status, G.I. Georg, T.T. Chen, I. Ojima, D.M. Vyas, eds., ACS Symposium Series 583, Wash., D.C., pp. 81–97, at least as early as 1995.

A. Hoffman, W. Khan, J. Worapong, G. Strobel, D. Griffen, B. Arbogast, D. Barofsky, R.B. Boone, L. Ning, P. Zheng, L. Daley, Bioprospecting for Taxol in Angiosperm Plant Extracts, Using High Performance Liquid Chromatography—Thermospray Mass Spectrometry to Detect the Anticancer Agent and Its Related Metabolites in Filbert Trees, Spectroscopy, vol. 13, No. 6, pp. 22–32, at least as early as Jun. 1998.

Gary Strobel, Xianshu Yang, Joe Sears, Robert Kramer, Rajinder S. Sidhu, and W.M. Hess, "Taxol from Pestalotiopsis microspora, an endophytic fungus of Taxus wallachiana," Microbiology (1996), 142, pp. 435–440, printed in Great Britain.

* cited by examiner

*Primary Examiner*—Francisco Prats
(74) *Attorney, Agent, or Firm*—Karen Dana Oster

(57) ABSTRACT

Methods for obtaining taxanes from novel sources are disclosed. Angiosperms other than hazelnut and the gymnosperm ginkgo have been discovered to be sources of taxane, including paclitaxel. Taxane may also be obtained from fungal endophytes from these plants. Methods for optimizing the recovery of taxane from plant sources are disclosed in which a plant part is surface-sterilized before extracting taxane therefrom or before culturing fungal endophytes therefrom.

9 Claims, 7 Drawing Sheets

1  10-deacetyl Baccatin III: C-13 = OH; C-10 = OH

2  Baccatin III: C-13 = OH 3  7-epi-10 deacetyl Taxol: C7 = epimer; C-10 = OH

4  Cephalomannine: R1 = $C_4H_9$ 5  10-deacetyl Taxol: C-10 = OH

6  Paclitaxel (shown)

Table 3. Taxanes recovered from culture medium of fungi isolated from hazelnut cultivars

| Fungus number | Paclitaxel (μg/L) | Taxol-like compounds (μg/L) |
|---|---|---|
| UP H-1 | nd | nd |
| UP H-2 | nd | nd |
| UP H-3 | 0.02 ± 0.01* | 1.50 ± 0.78 |
| UP H-4 | 4.19 ± 2.29 | 4.97 ± 3.68 |
| UP H-5 | 0.87 ± 0.54 | 34.59 ± 9.12 |
| UP H-6 | nd | nd |
| UP H-7 | 1.94 ± 0.73 | 6.70 ± 1.91 |
| UP H-8 | nd | nd |
| UP H-9 | nd | nd |
| UP H-10 | 3.21 ± 1.42 | 32.16 ± 6.16 |
| UP H-11 | 2.50 ± 0.65 | 7.75 ± 1.39 |
| UP H-12 | 16.07 ± 1.14 | 42.23 ± 9.24 |
| UP H-13 | nd | nd |
| UP H-14 | 4.16 ± 0.79 | 28.47 ± 6.50 |
| UP H-15 | 6.45 ± 0.79 | 27.16 ± 6.82 |
| UP H-16 | nd | nd |
| UP H-17 | nd | nd |
| UP H-18 | nd | nd |
| UP H-19 | 0.50 ± 0.11 | 0.60 ± 0.09 |

* values ± SD
nd = below detection limit

Notes: Fungi were cultured in 100 mL of medium containing potato, hazelnut and 1 or 10 grams of glucose per liter; cultures grown for 10, 15, 20 or 30 days; "Taxol-like compounds" include paclitaxel and 10-deacetyl taxol (recoveries of cephalomannine and 7 epi, 10-deacetyl taxol were very small).

FIG. 2

METHODS FOR OBTAINING TAXANES

This application claims priority from pending provisional patent application No. 60/216,863, filed on Jul. 7, 2000.

FIELD OF THE INVENTION

The present invention is directed generally to methods for obtaining paclitaxel and other important taxanes from novel plant sources of taxanes. The present invention is also directed to methods for obtaining paclitaxel and other taxanes by culturing fungal endophytes of these novel sources.

BACKGROUND OF THE INVENTION

Paclitaxel is the active ingredient in the anticancer drug TAXOL® ("taxol") marketed by Bristol Myers Squibb. Taxol has been approved for treatment of ovarian and breast cancers, Kaposi's sarcoma, and non-small-cell lung cancer. It is also in clinical trial for treatment of several other cancers in combination with other chemotherapeutic agents. Several other uses for paclitaxel have been identified, including possible treatments for psoriasis, polycystic kidney disease, multiple sclerosis, and Alzheimer's disease. With the increasing number of uses, the need for new sources of paclitaxel is becoming ever more apparent.

Paclitaxel is a complex diterpenoid compound originally extracted from the bark of the Pacific yew tree, *Taxus brevifolia*. A number of related compounds, collectively known as "taxanes," are also found in the yew extract. Paclitaxel is currently obtained from various species of yew or is made by partial synthesis from other taxanes also obtained from yew. Taxanes other than paclitaxel are therefore of interest for medicinal use. The chemical structures of six taxanes are shown in FIG. 1.

Yields of taxanes from yew are generally quite small (on the order of milligrams per kilogram of dried plant material). At the present time, there may be enough paclitaxel for FDA-approved uses in chemotherapy. As the numerous clinical trials involving this compound draw to a close, however, it is clear that demand for paclitaxel will increase. Accordingly, it is important to identify alternative sources for this compound.

Laboratory (chemical) synthesis of paclitaxel has been reported from groups led by Holton, Nicolaou, Wender, and Danis hefsky and in patent references directed to chemical synthesis of paclitaxel and other taxanes, or to taxane precursors of paclitaxel:

U.S. Pat. No. 4,468,458 to Sato et al. entitled Two-Functional-Group Terpenoids, Preparation, and Anti-Ulcer Agents.

U.S. Pat. No. 4,814,470 to Colin et al. entitled Taxol Derivatives, Their Preparation, and Pharmaceutical Compositions.

U.S. Pat. No. 4,857,653 to Colin et al. entitled Process for the Preparation of Taxol and 10-Deacetyltaxol.

U.S. Pat. No. 4,924,011 to Denis et al. entitled Process for Preparing Taxol.

U.S. Pat. No. 4,960,790 to Stella et al. entitled Derivatives of Taxol, Pharmaceutical Compositions, and Preparation.

U.S. Pat. No. 5,202,448 to Carver et al. entitled Processes of Converting Taxanes Into Baccatin III.

U.S. Pat. No. 5,232,684 to Blumberg et al. entitled Labeled Resiniferatoxin, Compositions Thereof, and Methods for Using.

U.S. Pat. No. 5,243,045 to Holton et al. entitled Certain Alkoxy Substituted Taxanes and Pharmaceutical Compositions.

Another reference, U.S. Pat. No. 6,043,072 to Croteau et al. entitled Nucleic Acids Encoding Taxus Geranylgeranyl Diphosphate Synthase, claims a nucleic acid sequence and genetic technology for creating nucleic acid sequences that code for taxanes. Many of these syntheses, however, are too complex and costly for commercial use. Accordingly, these syntheses are not a practical method for supplying enough of the drug for all patients. Other references claim cancer treatment methods using taxanes:

U.S. Pat. No. 4,206,221 to Miller et al. entitled Cephalomannine and Its Use in Treating Leukemic Tumors.

U.S. Pat. No. 4,942,184 to Haugwitz et al. entitled Water-Soluble, Antineoplastic Derivatives of Taxol.

U.S. Pat. No. 5,958,741 to Stierle et al. entitled Taxol Production by a Microbe.

Twelve references claim methods for recovering taxanes from plant tissue or from microorganisms obtained from plant tissue:

U.S. Pat. No. 5,019,504 to Christen et al. entitled Production of Taxol or Taxol-like Compounds in Cell Culture.

U.S. Pat. No. 5,322,779 to Strobel et al. entitled Taxol Production by Taxomyces Andreanae.

U.S. Pat. No. 5,445,809 to Strobel et al. entitled Production of Taxol From the Yew Tree.

U.S. Pat. No. 5,451,392 to Strobel et al. entitled Production of Taxol.

U.S. Pat. No. 5,670,663 to Durzan et al. entitled Recovery of Taxanes From Conifers.

U.S. Pat. No. 5,861,302 to Stierle et al. entitled Taxol Production by a Microbe.

U.S. Pat. No. 5,908,759 to Stierle et al. entitled Taxol Production by a Microbe.

U.S. Pat. No. 5,916,783 to Stierle et al. entitled Taxol Production by a Microbe.

U.S. Pat. No. 5,981,777 to Durzan et al. entitled Recovery of Taxanes From Plant Material.

U.S. Pat. No. 6,013,493 to Stierle et al. entitled Taxol Production by a Microbe.

U.S. Pat. No. 6,030,818 to Pagé et al. entitled Bacterial Mass-Production of Taxanes.

U.S. Pat. No. 6,066,748 to Han et al. entitled Process of Extracting TAXOL® From Taxus Cuspidata.

Researchers such as Strobel, Stierle, Han, and Pagé have shown that several of the bacteria and fungi native to yew trees are capable of making paclitaxel and suggest that fungal cultures may be a viable alternative source for paclitaxel. A number of other bioreactive compounds have also been obtained from plant endophytes isolated from yew and related species.

The following references describe generally the work done by Drs. Strobel and Stierle and their colleagues, which was limited to plants (yew trees) within the genus Taxus:

Stierle, A., G. Strobel, D. Stierle (1993) Taxol and taxane production by *Taxomyces andreanae*, an endophytic fungus of Pacific Yew. *Science* 260:214–216.

Strobel, G., X. Yang, J. Sears, R. Kramer, R. S. Sidhu, W. M. Hess (1996) Taxol from *Pestalotiopsis microspora*, an endophytic fungus of *Taxus wallachiana*. *Microbiology* 142:435–440.

Stierle, A., D. Stierle, G. Strobel, G. Bignami, P. Grothaus (1995) Bioactive metabolites of the endophytic fungi of pacific yew, *Taxus brevifolia*: paclitaxel, taxanes, and other bioactive compounds. In: *Taxane Anticancer Agents: Basic Science and Current Status*. G. I. Georg, T. T. Chen, I. Ojima, D. M. Vyas, eds. ACS Symposium Series 583, Wash. D.C., pp. 81–97.

U.S. Pat. No. 5,451,392 to Strobel et al. entitled Production of Taxol.

U.S. Pat. No. 5,445,809 to Strobel et al. entitled Production of Taxol From the Yew Tree.

U.S. Pat. No. 5,322,779 to Strobel et al. entitled Taxol Production by *Taxomyces Adreanae*.

U.S. Pat. No. 6,013,493 to Stierle et al. entitled Taxol Production by a Microbe.

U.S. Pat. No. 5,958,741 to Stierle et al. entitled Taxol Production by a Microbe.

U.S. Pat. No. 5,916,783 to Stierle et al. entitled Taxol Production by a Microbe.

U.S. Pat. No. 5,908,759 to Stierle et al. entitled Taxol Production by a Microbe.

U.S. Pat. No. 5,861,302 to Stierle et al. entitled Taxol Production by a Microbe.

Other researchers, such as Don J. Durzan and Frank Ventimiglia, discovered taxane-producing plants outside of the genus Taxus but still within the botanical order containing the genus Taxus. U.S. Pat. No. 5,670,663 to Durzan et al. (the "Durzan reference") is directed to recovery of taxanes from conifers. The Durzan reference is significant for broadening the state of the art with regard to plant species from which taxanes may be obtained. Before the work of Durzan et al., it was thought that taxanes could be obtained only from plants of the genus Taxus. The Durzan reference suggested that taxane-producing plants are limited to gymnosperms of the order of conifers, including the genus Taxus. Neither the work of Strobel and Stierle et al. nor the work of Durzan et al. suggests that taxanes could ever be discovered in angiosperms or in other gymnosperms.

Background information on the inventor's work may be found in the following publication coauthored by the inventor:

Hoffman, A., W. Khan, J. Worapong, G. Strobel, D. Griffen, B. Arbogast, D. Barofsky, R. B. Boone, L. Ning, P. Zheng, L. Daley (1998) Bioprospecting for Taxol in angiosperm plant extracts: Using high performance liquid chromatography-thermospray mass spectrometry to detect the anticancer agent and its related metabolites in filbert trees. *Spectroscopy* 13:22–32.

Finally, the following references generally describe various aspects of the art:

Wani, M. C., W. H. Taylor, M. E. Wall, P. Coggon, A. T McPhail (1971) Plant antitumor agents. VI. The isolation and structure of taxol, a novel antileukemic and antitumor agent from *Taxus brevifolia*. *J. Am. Chem. Soc.* 93:2325–2327.

Difco Laboratories (1953) Difco Manual of Dehydrated Culture Media and Reagents for Microbiological and Clinical Laboratory Procedures, $9^{th}$ ed., pp. 64–65 and 242–246. Difco Laboratories, Detroit, Mich.

Each of the above scientific and patent references is incorporated into this application in its entirety by reference.

Taxanes have been isolated from various conifers, by Strobel and Stierle, among others. According to the method of Strobel and Stierle for isolating taxanes, plant material from the taxane-producing conifer is ground, and the taxane is isolated from this ground plant material. This method has the disadvantages of low yield and the introduction of contaminants from the surface of the plant material. A method for isolating a taxane from plant material that overcomes these disadvantages is needed.

As discussed above, taxanes were first discovered in yew trees of the genus Taxus. Later, other researchers determined that taxanes are also produced in other conifers and in particular strains of hazelnut trees of the genus Corylus, a member of the order of angiosperms, plants that produce seeds. See Hoffman et al., above. To date, hazelnut is the only angiosperms in which taxanes have ever been found to be produced.

Strobel and Stierle further disclosed that taxanes may be isolated from a certain endophytic fungus, *Taxomyces andreanae*, that lives within yew trees. Strobel and Stierle later disclosed that several other endophytic fungi of yew trees produce taxanes. Likewise, Hoffman et al. disclose that endophytic fungi from the hazelnut strains that produce taxanes themselves produce taxanes when grown in culture.

Because taxanes are produced in very low concentrations in these sources, a significant need exists to find other sources of taxanes if possible, especially of paclitaxel.

SUMMARY OF THE INVENTION

In this specification, the term "taxane" refers generally to any or all of the taxanes, a known class of chemical compounds having antitumor properties, whether now known or discovered in the future. The use of any specific taxane, such as "paclitaxel," refers solely to that particular taxane.

The present invention is directed generally to methods for obtaining paclitaxel and other important taxanes from novel plant sources. The present invention is also directed to methods for obtaining paclitaxel and other taxanes by culturing fungal endophytes of these novel sources.

It has been discovered that the yield of taxanes isolated from plant material from a plant that produces taxanes may be increased by sterilizing the surface of the plant material before extracting the taxane. It has been further discovered that the yield of taxanes that is isolated from such plant material may be increased by not grinding the plant material before extracting. Preferably, the plant material is surface-sterilized and is not ground before the extraction of taxanes.

One embodiment of the invention is a method for extracting a taxane from a part of a taxane-producing plant. The method of the invention includes sterilizing the surface of the plant part before extracting the taxane.

In another embodiment, the invention is a method for extracting a taxane from a part of a taxane-producing plant. The method of the invention omits grinding the plant part before extracting the taxane.

Preferably, the method of the invention includes sterilizing the surface of the plant part and omits grinding the plant part before extracting the taxane.

It has been discovered in accordance with the invention that taxanes are produced and may be isolated from angiosperms other than hazelnut trees of the genus Corylus. Surprisingly, the inventor has discovered that taxanes are produced in a wide variety of angiosperms. This exciting discovery opens the possibility for the first time that taxanes will be abundantly found in many species and that future supplies of taxanes will be available to meet expected future demand.

In another embodiment, the invention is a method for extracting a taxane from a plant part of an angiosperm other than a hazelnut tree. Preferably, the taxane is extracted from a part of the nonhazelnut angiosperm following surface sterilization of the part with or without grinding the part before the extraction of the taxane.

It has been further discovered that taxanes are produced by endophytic fungi of angiosperms other than those of hazelnut trees of the genus Corylus. This discovery is likewise an exciting one that opens the possibility that taxanes will be abundantly available to meet future needs.

In another embodiment, the invention is a method for obtaining taxane by culturing a taxane-producing fungus that is an endophyte of an angiosperm other than hazelnut of the genus Corylus and obtaining the taxane produced by the fungus. Preferably, the endophytic fungus is a fungus that is not a member of a taxonomic species that is an endophyte of a gymnosperm or of hazelnut. Most preferably, the endophytic fungus according to the method of the invention is of the genus Alternaria, a genus of fungus that has not until now been discovered to produce a taxane.

In another embodiment, the invention is a method for isolating a taxane-producing endophytic fungus from a plant. In accordance with this embodiment, a plant part is surface-sterilized before placing the plant part in contact with a growth medium capable of supporting fungal growth. Preferably, the plant part is not ground before contacting the plant part with the growth medium.

In another embodiment, the invention is a novel fungus that has been discovered to produce taxane.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 2 is a table showing taxanes recovered from culture medium of fungi isolated from hazelnut cultivars.

DETAILED DESCRIPTION OF THE INVENTION

Figure 1:
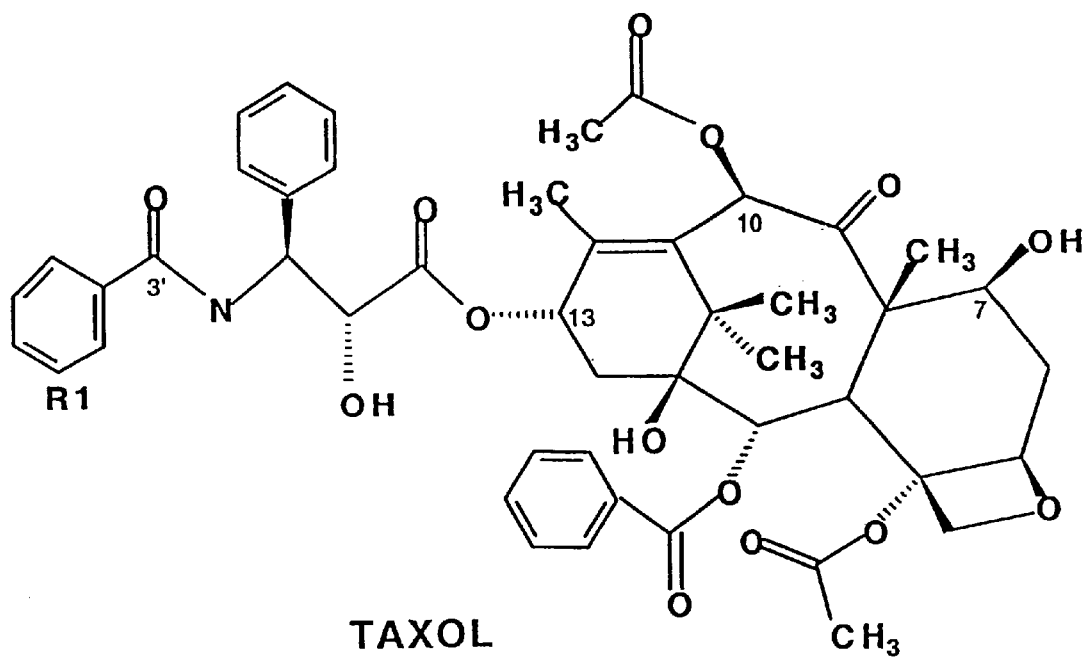
FIG. 1 is a diagram showing the structure of paclitaxel and five other common taxanes.

Prior art methods of extracting a taxane from a plant part include grinding the plant part and do not include sterilization of the plant part. In accordance with the method of the invention, it has been discovered that the yield of taxane extracted from a plant part is increased by omitting the grinding step, sterilizing the surface of the plant part, or both.

In accordance with a preferred method of the invention, the plant part from which taxane is to be extracted is surface-sterilized and then taxane is extracted. The precise manner in which the surface sterilization is achieved is immaterial. In a preferred embodiment, the plant part from which taxane is to be extracted is washed and rinsed to remove any dirt or debris, then is coated with or soaked in a disinfectant such as bleach or an alcohol such as ethanol or methanol. Preferably, the disinfection of the plant part is by a serial disinfection, such as by disinfecting with a bleach and then disinfecting with an alcohol, or with an alcohol followed by a bleach. Serial disinfection with different disinfectants maximizes the likelihood that all organisms on the surface of the plant part will be killed.

Plant parts that are suitable for the method of the invention for extracting taxane include all plant parts in which taxane produced by the plant is found. Examples of such parts include twigs, seeds, nuts, leaves, roots, shoots, and fruit.

If desired, following sterilization, the surface of the plant part may be removed, such as by stripping away the bark from the part or removing the seed covering. This step, however, is not essential for the method of taxane extraction according to the invention.

Preferably, whether or not the surface of the plant part is sterilized as described above, the plant part is not ground before the extraction of taxane, as is practiced in the prior art. Omitting grinding has been found to reduce contaminants and to increase the yield of taxane from plant parts containing taxane. Further, this omits a step from prior art methods of extracting taxane without reducing the efficiency of such methods.

In accordance with the invention, taxanes, such as paclitaxel, have been found to be produced in angiosperms other than hazelnut (Corylus spp.). For example, taxanes have been identified in plant parts of huckleberry (*Vacinium parvifolium*). Other examples of angiosperms other than hazelnut in which taxanes were found to be produced include Scotch broom (*Cytisus scoparius*) and red alder (*Alnus rubra*). The vast dissimilarity between these angiosperms indicates that the ability to produce taxanes is widely distributed among the angiosperms. Taxanes have also been determined to be produced in ginkgo (*Ginkgo biloba*), which, although it is a gymnosperm, is only distantly related to the conifers, in which taxane production had been previously identified.

Plants that are suitable for the method of the invention include any angiosperm, other than hazelnut, that is found to produce taxane. Such taxane-producing plants may be determined, for example, by extraction of taxane if present by methods such as disclosed in Hoffman et al., *Spectroscopy* 13(6):22–32 (1999), and then by determining whether taxane was indeed extracted, such as by chromatography like HPLC, or by immunologic methods like a competitive inhibition immunoassay (CIEIA). A CIEIA may be performed as disclosed in Hoffman et al., for example by using a taxol immunoassay kit (Hawaii Biotechnology Group, Aiea, Hi). Other taxane-producing plants that are suitable for the method of the invention include gymnosperms other than conifers and yew, such as ginkgo.

Any method now known in the art or later developed for extracting taxane from these novel plant sources of taxane is suitable for the method of the invention. Such methods may include grinding the plant part and may omit disinfection of the surface of the plant part. In a preferred method, a part of an angiosperm plant other than hazelnut, or a part of a ginkgo, is surface-sterilized and the taxane present in the part is extracted by any method known in the art or later developed. In another preferred embodiment, the taxane is extracted from the part of an angiosperm plant that produces taxane other than hazelnut or of ginkgo without grinding the part before the extraction of the taxane. In a most preferred method according to the invention, a plant part of an angiosperm that produces taxane, other than hazelnut, or of ginkgo is surface-sterilized and is not ground prior to extraction of taxane from the part.

In order to extract taxane from the plant part, plant tissue is put in contact with a composition that extracts taxanes. The extraction composition is preferably an organic solvent, including, for example, methanol, dichloromethane, and/or ethyl acetate. The extraction composition may also include a resin column or any other substance that removes taxanes from plant tissue. Agitation of the plant parts in the solvent may increase the yield of taxane or the rate of taxane extraction.

Endophytic fungi of taxane-producing plants that produce taxane, even independently from the plant, have been discovered. According to the invention, such fungi are endophytes of angiosperms that produce taxane, other than hazelnut, or of ginkgo. In a preferred embodiment, the endophytic fungus is of the genus Alternaria. The Alternaria sp. fungi of the invention may be endophytes of any plant, including gymnosperms, conifers, and yews. Other genuses of fungi, such as Taxomyces, Bispora, Xylaria, Micrococcus, and Penicillium, have been determined to produce taxanes; each of these fungi has been isolated from a yew or a conifer. Accordingly, fungi of the invention other than Alternaria are endophytes of ginkgo or of angiosperms other than hazelnut.

The characteristics of the genus Alternaria are well known in the art. Microscopically, Alternaria tend to have branched acropetal chains (blastocatenate) of multicelled conidia that are produced sympodially from simple, sometimes branched short or elongate conidiophores. Alternaria have no sexual spore stage; that is, they do not produce meiospores. Members of this genus do produce genetically identical spores (conidia) called mitospores. The conidia of Alternaria are obclavate, obpyriform, and sometimes ovoid or ellipsoidal, and they often have a short conical or cylindrical beak, giving the conidia its well-known clublike appearance. The conidia are pale brown, smooth-walled or verrucose, multicelled, and pigmented, and they are produced in simple or branching chains. Macroscopically, Alternaria colonies are black to ovilaceous-black or grayish, and are suedelike to floccose.

Three fungi that produce taxane and that have been determined to be members of the genus Alternaria have been deposited in accordance with the Budapest Treaty at the Agricultural Research Service Culture Collection (NRRL) and have been given the following NRRL designation numbers: 30404, 30406, and 30407. A fourth fungus that produces taxane is believed to be an Alternaria and has been given the NRRL designation number 30405. Each of these fungi was isolated from hazelnut tree parts.

In order to obtain taxane according to the invention, a pure culture of a fungus of the invention is cultured and permitted to grow and produce taxane. The taxane is then obtained from the fungus or from the culture medium in which or on which the fungus was grown.

The fungus from which taxane is obtained may be cultured directly from a plant in which the fungus lives as an endophyte, or it may be obtained from a culture, such as from agar in a petri dish. If the fungus is being cultured from a plant part, it is preferred as described above that the plant part be surface-sterilized and that the plant part not be ground before culturing. In a preferred embodiment, a plant part is surface-sterilized and placed on or into a culture medium that supports fungal growth. Preferably, the culture medium is a potato dextrose ("PD") agar, preferably supplemented with fungal growth nutrients, such as phenylalanine and acetate.

The invention is further described in the following non-limiting examples.

EXAMPLE 1

Extraction of Taxane From an Angiosperm Other Than Hazelnut

Axenic (sterile) cultures were established from leaves and bark of huckleberry shrubs. Taxanes were also recovered from these tissues, thus establishing the ability of huckleberry tissues to synthesize taxanes, including paclitaxel. The discovery that huckleberry plant cells could produce paclitaxel was unexpected and represented the first time that paclitaxel had been isolated from an angiosperm other than hazelnut.

Huckleberry plant material, including leaves, small branches, and berries, is ground to the consistency of coffee grounds. A portion of the ground material is dried in an oven at approximately 100° C. The remainder of the ground material is shaken in a vessel with an extraction solvent, such as methanol, for at least three periods of at least five minutes each. The extraction solvent is then filtered or centrifuged from the plant material.

The extraction solvent is evaporated from the filtrate or decanted liquid under reduced pressure in a water bath at 35° C. to 38° C. The evaporation residue is removed from the evaporation flask with sterile water and hexane. Strongly hydrophobic components of the mixture (including chlorophyll, fats, and oils) are extracted with hexane(s), pentane(s), or related solvents and discarded.

The more nonpolar of the remaining components are extracted from the aqueous solution by solid-phase extraction cartridges, for example, the C-18 Sep-Pak (Millipore). Strongly hydrophilic components, such as salts and sugars, pass through the cartridges and are discarded. The components that become attached to the solid-phase medium are rinsed off, using methanol, and retained.

Components of the retained mixture have solubility properties similar to those of paclitaxel and other taxanes. The solvents are evaporated, and the solids are dissolved in methanol and filtered to remove particles before component separation.

Figure 3:
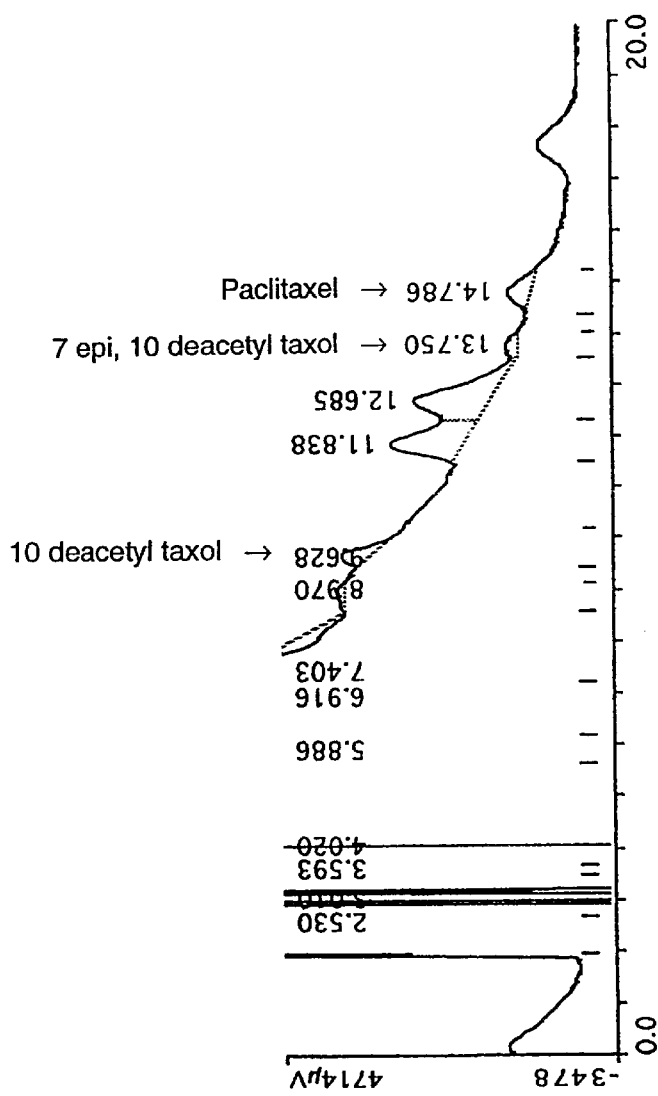
FIG. 3 is an HPLC chromatogram of extract from a hazelnut showing peaks corresponding to different taxanes.
Figure 4:
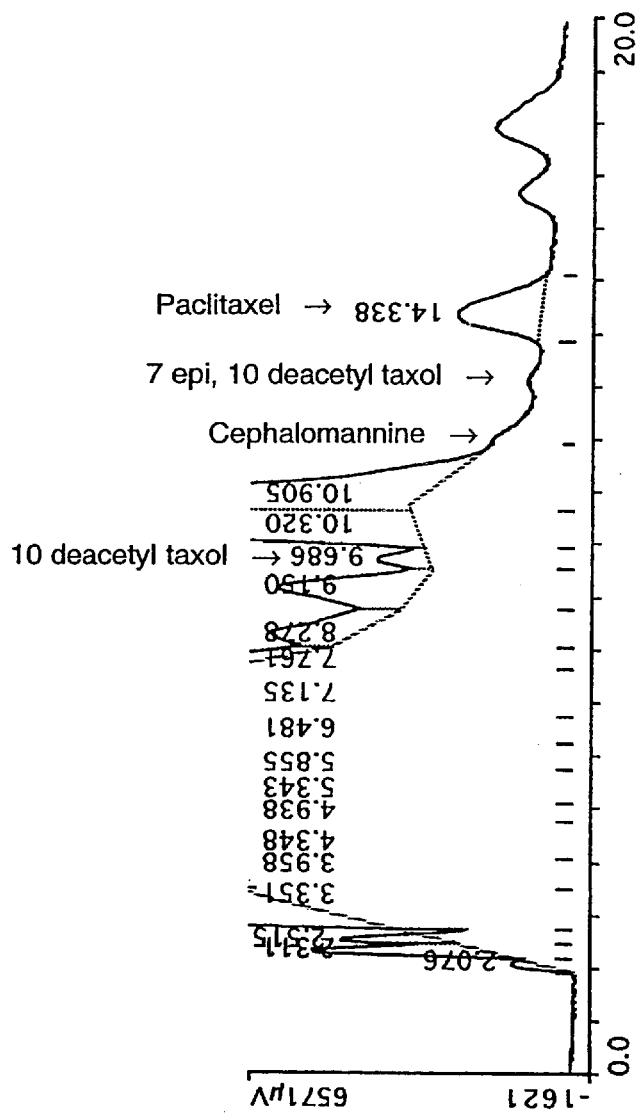
FIG. 4 is an HPLC chromatogram of extract of culture medium from fungal strain UPH-12, NRRL Accession No.30405.

The solid components dissolved in methanol are separated, using reverse-phase high-performance liquid chromatography ("HPLC") on a column designed to separate taxanes, and yielding results similar to those shown in FIGS. 3 and 4. In order to obtain "cleaner" samples of particular taxanes, the extracts are applied to silica-gel plates and separated by thin-layer chromatography ("TLC"). The standard bands for the various taxanes, as shown in Table 1, are scraped and dissolved from the silica gel.

TABLE 1

Separation of six taxanes by TLC on silica gel using 4 ethyl acetate: 1 hexane as eluant

| Taxane | rf |
|---|---|
| 10 deacetyl baccatin III | 0.33 |
| Baccatin III | 0.64 |
| 10 deacetyl taxol | 0.35 |
| Cephalomannine | 0.67 |

TABLE 1-continued

Separation of six taxanes by TLC on silica gel using 4 ethyl acetate: 1 hexane as eluant

| Taxane | rf |
|---|---|
| 7 epi 10 deacetyl taxol | 0.76 |
| Taxol | 0.71 |

EXAMPLE 2

Method for Isolating Fungi From Plant Material

The inventor has found that the success rate for discovering and obtaining taxane-producing fungal endophytes is determined in part by the technique used to isolate the fungal endophytes from a plant material. While Strobel and colleagues found approximately 1 taxane-producing fungus for every 200 samples, the preferred method of the present invention increases the success rate to 3 or 4 taxane-producing fungi for every 200 samples.

Suitable plant material includes leaves, stems, bark, roots, nuts, or other plant parts or products. First, the plant material is brushed thoroughly with soap to remove surface dirt and decrease surface tension. Next, the plant material is rinsed with tap water. Then the rinsed plant material is soaked separately in alcohol (70% ethanol) and bleach (20% commercial (hypochlorite) bleach) for up to 5 minutes each (in either order). The alcohol and/or bleach soaks may be repeated. The surface-sterilized plant material is then rinsed with sterile water. It is then cut into small pieces (0.5 to 1.0 cm in longest dimension) with a sterile scalpel and placed on solid water agar medium. This dual surface-sterilization technique kills contaminants more effectively than ethanol or bleach treatments singly.

Fungal hyphae usually begin to grow from the plant material after two days. Pure cultures are obtained when tips of fungal hyphae are removed soon after they appear.

Newly removed hyphal tips are placed on a commercially or locally prepared mycological agar preparation. Commonly used preparations include PD agar or broth, mycological agar or broth, malt agar or broth, and Czapek agar or broth (Difco Manual).

When a fungal culture appears by visual inspection to be pure, segments of the solid culture are placed in mycological broth preparations. The fungi is incubated for one to three weeks at temperatures from 20° C. to 26° C. in ambient light. Fungi that are isolated as disclosed in this example are indicated in FIG. 2.

EXAMPLE 3

Obtaining Taxane From Taxane-producing Endophytic Fungi From an Angiosperm Other Than Hazelnut Small branches of about 1 cm diameter or less, with leaves, are cut from a huckleberry plant. The small branches are thoroughly cleaned with a brush and soap, for example, Ivory® (Procter and Gamble, Cincinnati, Ohio) bar soap and a toothbrush. After this, they are gently stirred in 70% ethanol for at least five minutes and gently stirred in 20% hypochlorite bleach for at least five minutes (in either order). The stirring in ethanol and bleach may be repeated once or twice in any order. The branches are aseptically cut into segments small enough to fit into a sterile petri dish, such as a 100-mm sterile petri dish, and are thoroughly rinsed with sterile distilled water.

Small pieces of leaf, petiole, and bark from the above surface sterilization and cutting procedure are removed and placed on the surface of sterile water agar in a petri dish. The dish is closed with a strip of Parafilm and left to incubate for two to six days. Small mycelial growths are removed from the edges of some of the plant pieces and placed on PD agar media.

Each fungal culture from the PD agar media is checked for purity, and after it is clear that a fungal culture is not contaminated, a description of its growth on solid medium is recorded. A second petri-dish culture may be started from a small piece of each previous culture.

A 1 to 2 cm$^2$ piece of each fungus is placed in 100 ml of liquid culture medium and allowed to grow for approximately three weeks while being gently and continuously shaken (50-rpm motion) at room temperature (approximately 21–26° C.) under ambient indoor light.

A description of each liquid culture is recorded at this time, and the mycelia are filtered from the liquid. The liquid is extracted approximately four times with 25 to 30 ml of dichloromethane or ethyl acetate in a separatory funnel. Extraction solvent may be added at a proportion approximately 1/3 to 1/4 the volume of the culture medium being extracted. The extractions are pooled and dried with anhydrous sodium sulfate before evaporation under reduced pressure at 35° C. to 38° C. The residue is then dissolved in a small known quantity of solvent, preferably methanol.

The residue dissolved in methanol is filtered through a 0.2-$\mu$m filter and separated using HPLC. If there is a peak at the retention times expected for one or more desired taxanes, a culture is saved as a taxane-producing culture. Other methods of analysis include but are not limited to HPLC-mass spectroscopy, nuclear magnetic resonance, immunoassay, and bioassay.

If taxane-producing fungi are grown on solid medium, photographs are taken of the growth habit of the fungi and of their mycelia stained with lactophenol cotton blue.

EXAMPLE 4

Identification of Taxane-producing Fungi

Several different fungi are isolated from hazelnut plant material. Of these fungi, several are selected to be tested for the production of paclitaxel and other taxanes. Eight fungal cultures are found to make measurable amounts of paclitaxel and other taxanes.

Paclitaxel and other taxanes are tentatively identified in extractions from culture media using HPLC retention times of authentic standards. Positive identification is based on mass spectra obtained by HPLC-thermospray mass spectrometry and/or proton or $^{13}$Carbon nmr (FIGS. 3 and 4).

Not all the taxanes shown in FIG. 1 are positively identified in each culture, but each of the cultures in which taxane is present contains paclitaxel. For the two fungi featured in Table 2, best results are obtained on medium containing ordinary PD broth and 0.6 grams of phenylalanine (Phe) per liter.

TABLE 2

Three taxanes (_g per liter) extracted from fungi numbers UPH-4 and UPH-14 grown on various media for three weeks.

| | 10 deacetyl taxol | Cephalomannine | Taxol |
|---|---|---|---|
| UPH-4 | | | |
| PD | 0.09 | 0.08 | 2.15 |

TABLE 2-continued

Three taxanes (_g per liter) extracted from fungi numbers
UPH-4 and UPH-14 grown on various media for three weeks.

|  | 10 deacetyl taxol | Cephalomannine | Taxol |
|---|---|---|---|
| PD + Phe | 1.33 | 0.06 | 6.22 |
| ½ PD + Phe | 4.51 | Nd | 3.16 |
| ½ PD + hazelnut + Phe | 0.50 | Nd | 2.54 |
| UPH-14 |  |  |  |
| PD | Nd | Nd | 0.36 |
| PD + Phe | 0.07 | 48.63 | 7.95 |
| ½ PD + Phe | Nd | Nd | 3.65 |
| ½ PD + hazelnut + Phe | 10.6 | Nd | 0.61 | nd - "below the detection limit of the instrument"
Values are averages of two or three trials.

EXAMPLE 5

Description of Some of the Recovered Fungi

A selected collection of paclitaxel-producing fungi, tested as above and described further below, is deposited with the Agricultural Research Service Culture Collection (NRRL) in Peoria, Ill. 61604, U.S.A., under the terms of the Budapest Treaty.

Figure 7:
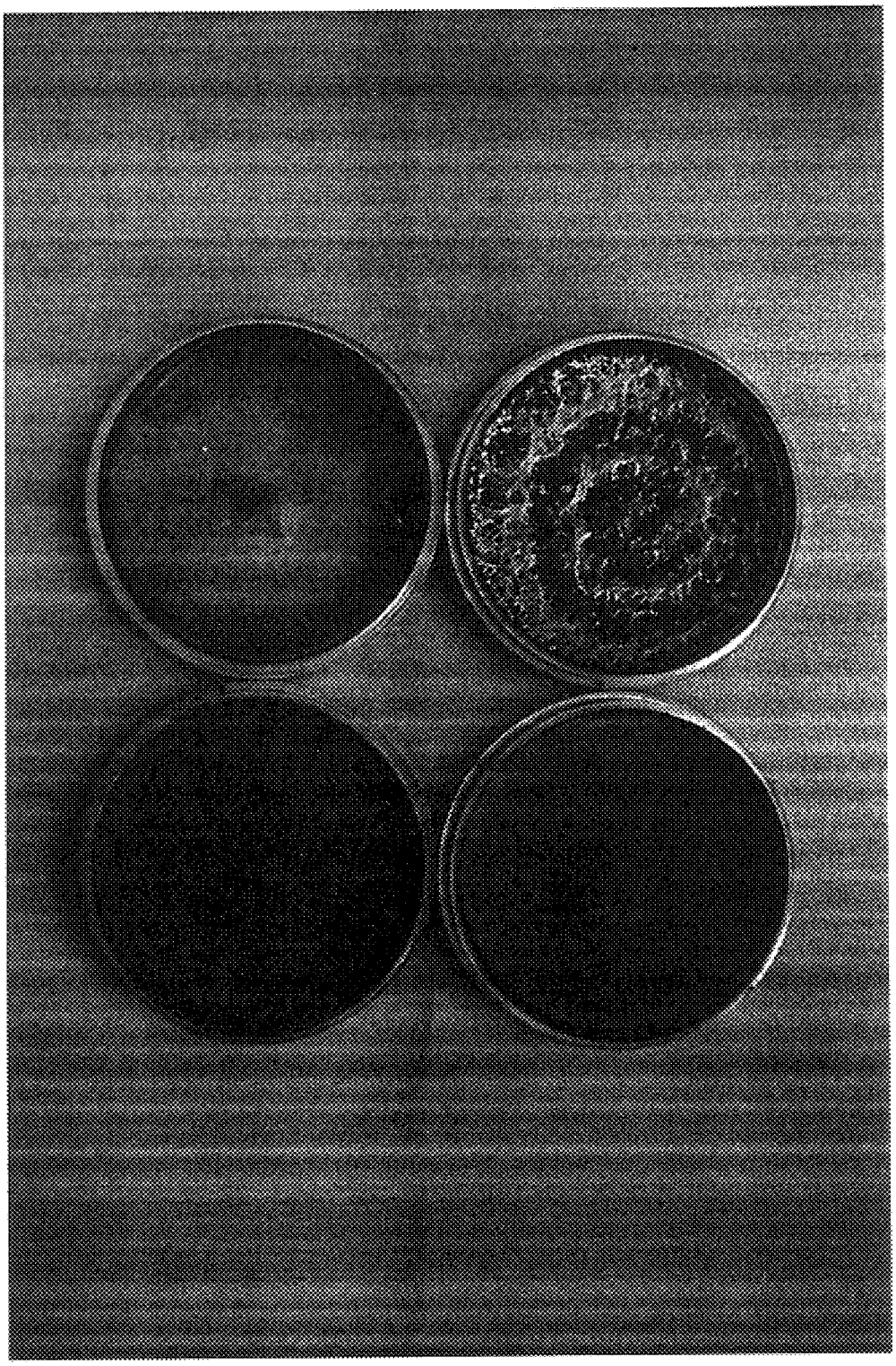
FIG. 7 is a photograph of cultures of, clockwise from upper left, UPH-12 (NRRL Accession No. 30405); UPH-15 (NRRL Accession No. 30407); UPH-14 (NRRL Accession No. 30406); and UPH4 (NRRL Accession No. 30404). UPH-4, UPH-14, and UPH-15 show the characteristic typical of Alternaria spp. UPH-12 is believed to be an Alternaria, but this has not yet been confirmed.

1. UPH-4: As shown in FIG. 7. Deposited at the NRRL and assigned Accession No. NRRL 30404.

At a growth temperature of 20–22° C., an isolated colony filled the surface of agar in a 35-mm petri dish in about a week. The color began as very light tan and eventually became tannish gray, lighter in the center and grayer toward the outer edges. The agar around the edges of growth became tan. No fruiting bodies were observed. This fungal isolate was identified as an Alternaria.

2. UPH-12: As shown in FIG. 7. Deposited at the NRRL and assigned Accession No. NRRL 30405.

At a growth temperature of 20–22° C., an isolated colony filled a 35-mm petri dish in about a week. The color began as off-white and developed white tufts in concentric circles on a pink background. The underside of the plate became very dark pink. No fruiting bodies were observed.

Figure 5:
FIG. 5 is a photomicrograph of fungal strain UPH-14, NRRL Accession No. 30406, showing a conidial structure typical of the genus Alternaria.

3. UPH-14: As shown in FIGS. 5 and 7. Deposited at the NRRL and assigned Accession No. NRRL 30406.

At a growth temperature of 20–22° C., an isolated colony filled a 35-mm petri dish in 7 to 9 days. The color began as a pale tan and progressed to become a uniform brown. The underside of the plate was black. The surface texture of the fungal growth was velutinous. Conidiophores were oval, brown, with septate conidia. See FIG. 5.

Figure 6:
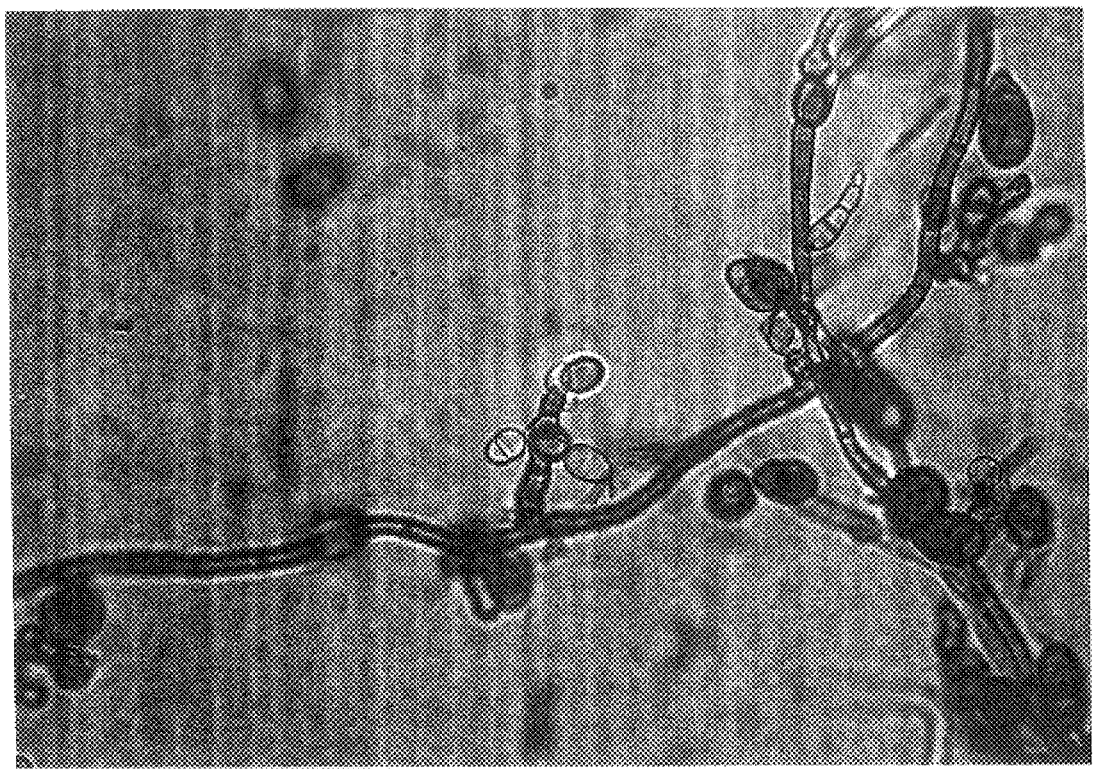
FIG. 6 is a photomicrograph of fungal strain UPH-15, NRRL Accession No. 30407, showing a conidial structure typical of the genus Alternaria.

4. UPH-15: As shown in FIGS. 6 and 7. Deposited at the NRRL and assigned Accession No. NRRL 30407.

At a growth temperature of 20–22° C., an isolated colony filled a 35-mm petri dish in 7 to 9 days. The color began as white or light tan and became progressively more gray. The underside of the plate was brown. The surface texture of the fungal growth was velutinous. Conidiophores were rounded oval, brown, with septate conidia. See FIG. 6.

EXAMPLE 6

Storage of Fungi and Standardization of Culture Inoculum

Approximately 10–15 grams of fungal mycelium from a liquid culture are ground in a large vial with 5 ml of sterile 80% glycerol with a sterile homogenizer. The mixture is stored at −80° C. The fungi retain viability for at least a year. This mixture is used to inoculate liquid culture broth or agar plates.

New fungal cultures are inoculated with a standardized amount of mycelium, 3 ml of inoculum (mycelium) per liter of culture broth.

EXAMPLE 7

Culture Medium and Conditions for Culturing Fungi

The present invention is also directed to optimal culture media and other growing conditions for taxane-producing fungi. Various taxane-producing fungi have different requirements for optimum growth and optimum taxane production. The following optimum growing conditions for taxane-producing fungi are experimentally determined:

Temperature: optimum growth occurs when the growing temperature is from 20 to 26° C.

Culture media: best results are obtained using a modified PD medium. The basic recipe is: 200 grams of potato infusion solids and 20 grams of dextrose per liter, dissolved and autoclaved. The following variations also provide optimum growth for some taxane-producing fungi:

(a) 82 grams raw potato and 1 to 10 grams dextrose (glucose) with approximately 8 grams of ground plant material (from the type of plant of which the fungus is an endophyte) per liter are cooked until potato is soft, then filtered and autoclaved.

(b) 200 grams of potato infusion solids and 20 grams of dextrose are dissolved and 6 grams of ground plant material are added before autoclaving. The solid is not removed.

(c) 100 grams of potato infusion solids and 10 grams of dextrose are dissolved and autoclaved with or without adding 6 grams of ground plant material.

(d) Commercial PD broth or agar is prepared according to directions.

(e) Filter-sterilized phenylalanine (0.6 grams) is added to a liter of any of the above media after autoclaving.

(f) 1.5% agar is added to any of the growth media described above.

(g) Mycological agar or broth, malt agar or broth, and Czapek agar or broth are also used depending on the needs of the specific fungi.

(h) Sucrose is substituted for dextrose; sodium, potassium, or ammonium acetate salts may be substituted for or used in addition to phenylalanine.

(i) Cornmeal replaces potato in any combination.

(j) 5 grams of sucrose per liter is added to any medium.

Light conditions: either ambient light or darkness is appropriate for most fungi.

Continuous gentle shaking accelerates the growth rate in liquid cultures for most fungi and therefore shortens the overall growth time.

EXAMPLE 8

A Typical Procedure for Fungal Isolation and Extraction of Taxanes, Exemplified With Hazelnut Small branches with leaves are cut from hazelnut cultivar "Ennis." They are thoroughly cleaned with a toothbrush and Ivory® bar soap. After this, they are gently stirred consecutively in 70% ethanol and 20% hypochlorite bleach for five minutes each. This is repeated once or twice more. After the branches are cut into segments small enough to fit into a sterile 100-mm petri dish, they are rinsed thoroughly with sterile distilled water.

Small pieces of leaf, petiole, and bark are removed and placed on the surface of sterile water agar in a petri dish. The dish is closed with a strip of Parafilm and left to incubate for about 2 to 6 days. Small mycelial growths are removed from the edges of some of the plant pieces and placed on PD agar.

After it is clear that the fungal culture is not contaminated, a description of its growth on solid medium is recorded. A second petri-dish culture is started from a small piece of each previous culture.

A 1 to 2 $cm^2$ piece of fungus is placed in 100 ml of liquid medium and allowed to grow for about three weeks while shaking at 125 rpm at room temperature in ambient light.

A description of the liquid culture is recorded, and the mycelium is filtered from the liquid. The liquid is extracted four times with 25 to 30 ml of dichloromethane in a separatory funnel. The pooled solvent is evaporated under reduced pressure, and the residue is dissolved in a small amount of methanol.

The methanol is filtered through a 0.2-$\mu$m filter and separated using HPLC. If there is a peak at the retention times expected for two or more of the six taxanes being monitored, the culture is saved. Two taxane-producing fungi are obtained from the Ennis material.

Photographs of the growth habit of the fungus on solid medium and mycelia stained with lactophenol cotton blue are taken for all taxane-producing fungi.

EXAMPLE 9

A Typical Procedure for Identifying Optimal Culture Conditions for Taxane-producing Fungi Taxane-producing fungi are grown on a variety of PD culture media. They are grown for about three weeks with shaking at 125 rpm and are harvested after log growth phase when the cultures stop growing. Not all fungi can be harvested after the same incubation time.

It is unlikely that the amount of plant material added to the culture medium provides the taxanes obtained from the fungal cultures. The amount of paclitaxel in the plant material added to the medium is very small compared with the amount recovered. The addition of the plant material does not correlate well with taxane yield.

Not all six taxanes can be identified in these cultures, but they all contain paclitaxel. Best results appear to be obtained on medium containing ordinary PD broth and 0.6 grams of phenylalanine per liter.

The terms and expressions that have been employed in the foregoing specification are used as terms of description and not of limitation and are not intended to exclude equivalents of the features shown and described or portions of them. The scope of the invention is defined and limited only by the claims that follow.

What is claimed is:

1. A method for obtaining taxane comprising obtaining an endophytic fungus from an angiosperm selected from the group consisting of Scotch broom, red alder, and huckleberry, which fungus produces taxane, permitting said fungus to grow in a culture medium, and removing said taxane from said fungus or from said culture medium.

2. The method of claim 1, wherein said fungus is a member of the genus Alternaria.

3. The method of claim 1, wherein said taxane is paclitaxel.

4. A method for isolating a taxane-producing endophytic fungus from a plant selected from the group consisting of Scotch broom, red alder, and huckleberry, comprising obtaining a part of said plant, which part has an outer surface and which plant part contains an endophytic fungus, sterilizing said outer surface of said plant part, placing said surface-sterilized plant part in contact with a growth medium capable of supporting fungal growth, permitting said endophytic fungus to grow in or on said growth medium, and isolating said endophytic fungus.

5. The method of claim 4, wherein said endophytic fungus is a member of the genus Alternaria.

6. The method of claim 4, wherein said plant part is not ground before putting it in contact with said growth medium.

7. A method for obtaining taxane comprising obtaining a fungus from a plant selected from the group consisting of Scotch broom, red alder, and huckleberry, which fungus produces taxane, permitting said fungus to grow in a culture medium, and removing said taxane from said fungus or from said culture medium.

8. The method of claim 7, wherein said fungus is a member of the genus Alternaria.

9. The method of claim 7, wherein said taxane is paclitaxel.

* * * * *

UNITED STATES PATENT AND TRADEMARK OFFICE
CERTIFICATE OF CORRECTION

PATENT NO. : 6,638,742 B1
DATED : October 28, 2003
INVENTOR(S) : Hoffman

It is certified that error appears in the above-identified patent and that said Letters Patent is hereby corrected as shown below:

Column 1,
Line 46, delete "Danis hefsky", insert -- Danishefsky --.

Column 3,
Line 11, delete "Adreanae", insert -- Andreanae --.
Line 51, delete "A.T", insert -- A.T. --.

Column 4,
Line 10, delete "angiosperms", insert -- angiosperm --.

Column 5,
Line 53, delete "UPH4", insert -- UPH-4 --.

Column 6,
Line 59, delete "Hi", insert -- HI --.

Column 11,
Line 10, insert a blank line above the heading "UPH-14".

Signed and Sealed this

Twenty-third Day of March, 2004

JON W. DUDAS
*Acting Director of the United States Patent and Trademark Office*